US010301187B1

(12) United States Patent
Awad et al.

(10) Patent No.: US 10,301,187 B1
(45) Date of Patent: May 28, 2019

(54) **SYNTHESIS OF TITANIUM DIOXIDE NANOPARTICLES USING *CYMBOPOGON PROXIMIS***

(71) Applicant: KING SAUD UNIVERSITY, Riyadh (SA)

(72) Inventors: Manal Ahmed Gasmelseed Awad, Riyadh (SA); Khalid Mustafa Osman Ortashi, Riyadh (SA); Awatif Ahmed Hendi, Riyadh (SA); Wadha Khalaf Alenazi, Riyadh (SA); Ali Aldalbahi, Riyadh (SA)

(73) Assignee: King Saud University, Riyadh (SA)

( * ) Notice: Subject to any disclaimer, the term of this patent is extended or adjusted under 35 U.S.C. 154(b) by 0 days.

(21) Appl. No.: 16/153,479

(22) Filed: Oct. 5, 2018

(51) Int. Cl.
*C01G 23/053* (2006.01)
*C01G 23/08* (2006.01)
*B82Y 40/00* (2011.01)
*B82Y 30/00* (2011.01)

(52) U.S. Cl.
CPC ........... *C01G 23/053* (2013.01); *C01G 23/08* (2013.01); *B82Y 30/00* (2013.01); *B82Y 40/00* (2013.01); *C01P 2002/01* (2013.01); *C01P 2002/72* (2013.01); *C01P 2002/85* (2013.01); *C01P 2004/62* (2013.01)

(58) Field of Classification Search
CPC ...... C01G 23/053; C01G 23/08; B82Y 30/00; B82Y 40/00; C01P 2002/01; C01P 2002/72; C01P 2002/85; C01P 2004/62
See application file for complete search history.

(56) References Cited

U.S. PATENT DOCUMENTS 9,491,947 B1   11/2016   Awad et al.

FOREIGN PATENT DOCUMENTS

WO   2005/095031 A1   10/2005

OTHER PUBLICATIONS

Meramo, Samir I., et al. "Environmental assessment of a large-scale production of TiO2 nanoparticles via green chemistry." Chemical Engineering Transactions 70 (2018): 1063-1068.*
Sundrarajan et al., "Green synthesis of titanium dioxide nanoparticles by Nyctanthes arbor-tristis leaves extract," Chalcogenide Letters, 8, 8, 2011, p. 447-451.
Venkatesh et al., "Facile one-step synthesis of novel TiO2 nanocoral by sol-gel method using Aloe vera plant extract," Indian Journal of Physics, 89 (5), 2015, p. 445-452.
Gopinath et al., "Eco-friendly synthesis of TiO2, Au and Pt doped TiO2 nanoparticles for dye sensitized solar cell applications and evaluation of toxicity," Superlattices and Microstructures, 92, 2016, p. 100-110.

(Continued)

Primary Examiner — Richard M Rump
(74) Attorney, Agent, or Firm — Richard C. Litman

(57) ABSTRACT

Synthesis of titanium dioxide ($TiO_2$) nanoparticles (NPs) includes mixing *Cymbopogon proximis* (Maharayb) grass extract with Titanium (IV) isopropoxide (TTIP). The synthesis is simple and occurs at a rapid rate. The synthesized $TiO_2$ nanoparticles can be effective in degrading Rhodamine B dye under UV light irradiation. Accordingly, the $TiO_2$ nanoparticles can be useful in purifying drinking water.

6 Claims, 4 Drawing Sheets

(56) References Cited

OTHER PUBLICATIONS

Shankar et al., "Controlling and optical properties of lemongrass extract synthesized gold nanotriangles and potential application in infrared-absorbing optical coatings," Chemistry of Materials, 17 (3), 2005, p. 566-572.

Masurkar et al., "Rapid biosynthesis of silver nanoparticles using *Cymbopogon citratus* (lemongrass) and its antimicrobial activity," Nano-Micro Letters, 3 (3), 2011, p. 189-194.

Murugan et al., "Cymbopogon citratus-synthesized gold nanoparticles boost the predation efficiency of copepod Mesocyclops aspericomis against malaria and dengue mosquitoes," Experimental Parasitology, 153, 2015, p. 129-138.

* cited by examiner

SYNTHESIS OF TITANIUM DIOXIDE NANOPARTICLES USING *CYMBOPOGON PROXIMIS*

BACKGROUND

1. Field

The disclosure of the present patent application relates to synthesis of titanium dioxide nanoparticles, and particularly, to synthesis of titanium dioxide nanoparticles using *Cymbopogon proximis*.

2. Description of the Related Art

In recent years, titanium dioxide has found wide use in several industries because of its physical and chemical properties in various states, nontoxicity, high stability, and simple preparation. In particular, catalytically active $TiO_2$ has been a subject of considerable attention due to its optical properties, chemical stability, non-toxicity, and high photo-activity. Furthermore, photocatalytic $TiO_2$ has been used as an antiviral and antibacterial agent, for the destruction of cancer cells, for decomposition of volatile organic compounds, and water splitting. $TiO_2$ is essential in medical and dental research due to its favorable properties, i.e., biocompatibility and low reactivity. For example, $TiO_2$ is used in the construction of dental implants and hollow drug-containing structures. $TiO_2$ nanotubes have been used for gradual drug release delivery systems.

One of the most important actual applications of $TiO_2$ lies in the field of renewable energy conversion and storage. For example, design of suitable catalytic materials such as $TiO_2$ for hydrogen production can provide a significant cost reduction in both hydrogen and auxiliary systems.

SUMMARY

Synthesis of titanium dioxide ($TiO_2$) nanoparticles (NPs) according to the present teachings includes mixing *Cymbopogon proximis* (Maharayb) grass extract with Titanium (IV) isopropoxide (TTIP). The synthesis is simple and occurs at a rapid rate. The synthesized $TiO_2$ nanoparticles can be effective in degrading Rhodamine B dye under UV light irradiation. Accordingly, the $TiO_2$ nanoparticles can be useful in purifying drinking water.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Synthesis of titanium dioxide ($TiO_2$) nanoparticles (NPs) according to the present teachings includes preparing an extract of *Cymbopogon proximis* (Maharayb), mixing the *Cymbopogon proximis* (Maharayb) grass extract with Titanium (IV) isopropoxide (TTIP) to obtain a paste, forming a powder from the paste, and calcinating the powder to provide the $TiO_2$ nanoparticles. The $TiO_2$ nanoparticles can have an average size of about 168.8 nm.

According to an exemplary embodiment, the $TiO_2$ nanoparticles can be prepared by grinding *Cymbopogon proximis* grass to provide a ground grass, adding water to the ground grass to provide a mixture, filtering the mixture to obtain a filtrate, combining the filtrate with titanium (IV) isopropoxide (TTIP) to obtain a brown solution, heating the brown solution, e.g., at a temperature of about 80° C., to obtain a paste; forming a powder from the paste, e.g., by pounding the paste, and calcinating the powder to provide the $TiO_2$ nanoparticles. For example, about 100 grams of grass can be ground and combined with about 100 ml of boiled, distilled water. A ratio of TTIP to filtrate can be about 2:1. The powder can be calcinated in a muffle furnace at about 400° C.

The synthesized $TiO_2$ nanoparticles can be effective in degrading Rhodamine B dye under UV light irradiation. For example, the $TiO_2$ nanoparticles can achieve about 100% removal of dye from dye-contaminated water when contacted with the water and exposed to about 50 hours of irradiation with UV light. Accordingly, the $TiO_2$ nanoparticles can be useful in purifying water.

The following examples illustrate the present teachings.

EXAMPLES

Example 1

Synthesis of $TiO_2$ Nanoparticles 100 g of *Cymbopogon proximis* (Maharayb) grass was washed, dried and ground. Then 100 ml boiled distilled water was added to the ground grass. The extract was filtered and the combined filtrates were used for preparation of the nanoparticles. Titanium (IV) isopropoxide (TTIP) and *Cymbopogon proximis* (Maharayb) extract were mixed together at a ratio of 2:1 under stirring until a brownish paste solution was formed. Then, the solution was heated on a hot plate at 80° C. The obtained paste was pulverized into powder from and calcinated in a muffle furnace at 400° C. The resulting beige brown powder contained $TiO_2$ nanoparticles.

Figure 1:
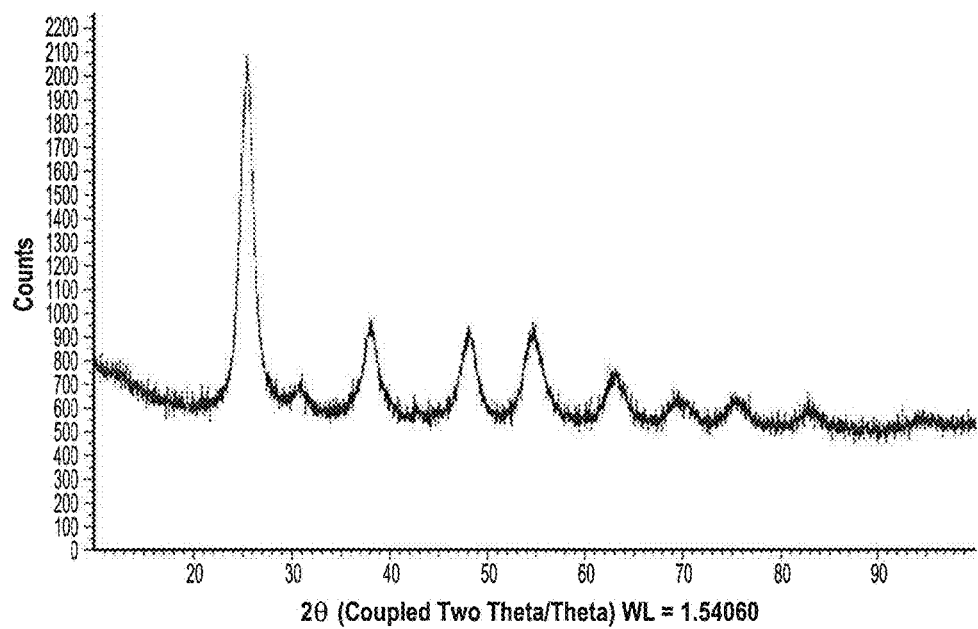
FIG. 1 shows the XRD analysis for the $TiO_2$ nanoparticles according to the present teachings.
Figure 2A:
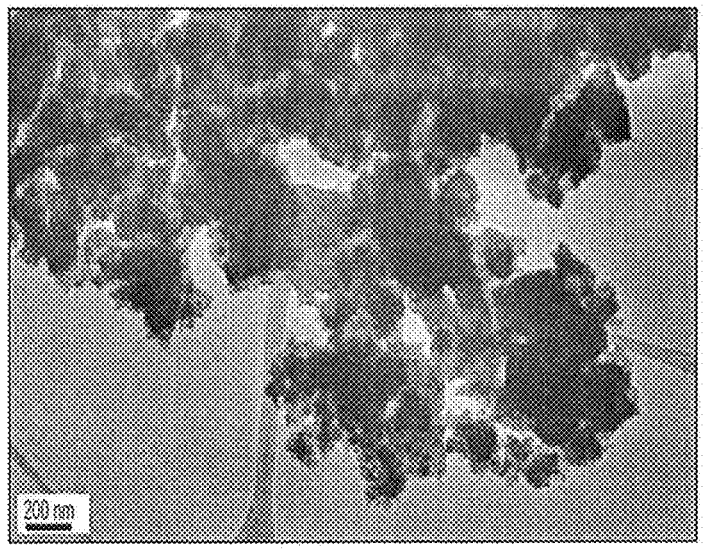
FIGS. 2A-2C show transmission electron microscope (TEM) images of $TiO_2$ nanoparticles according to the present teachings.
Figure 2B:
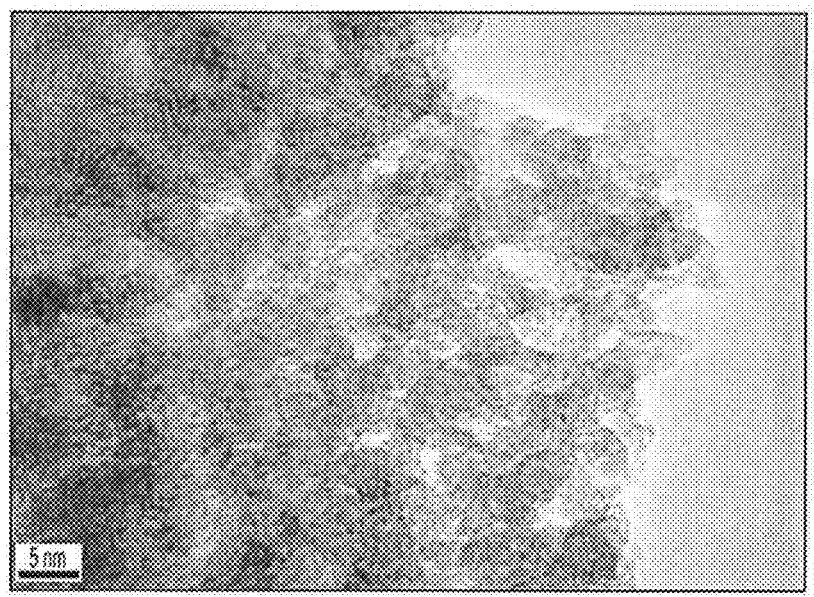
Figure 2C:
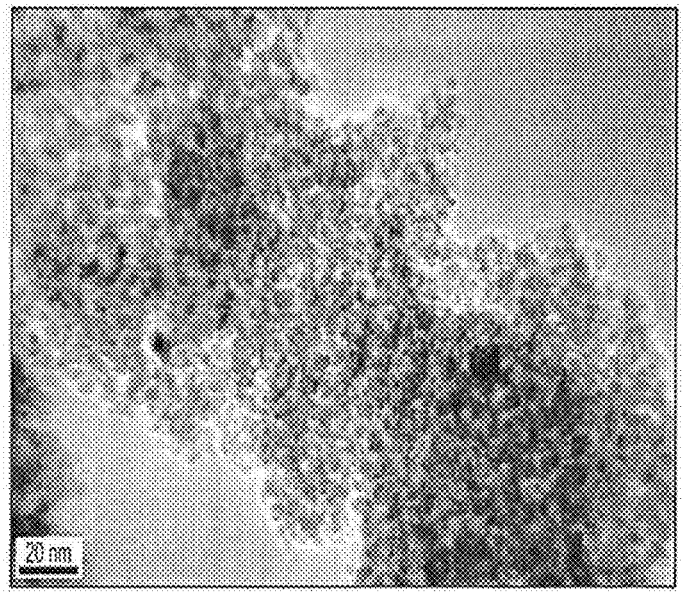
Figure 3:
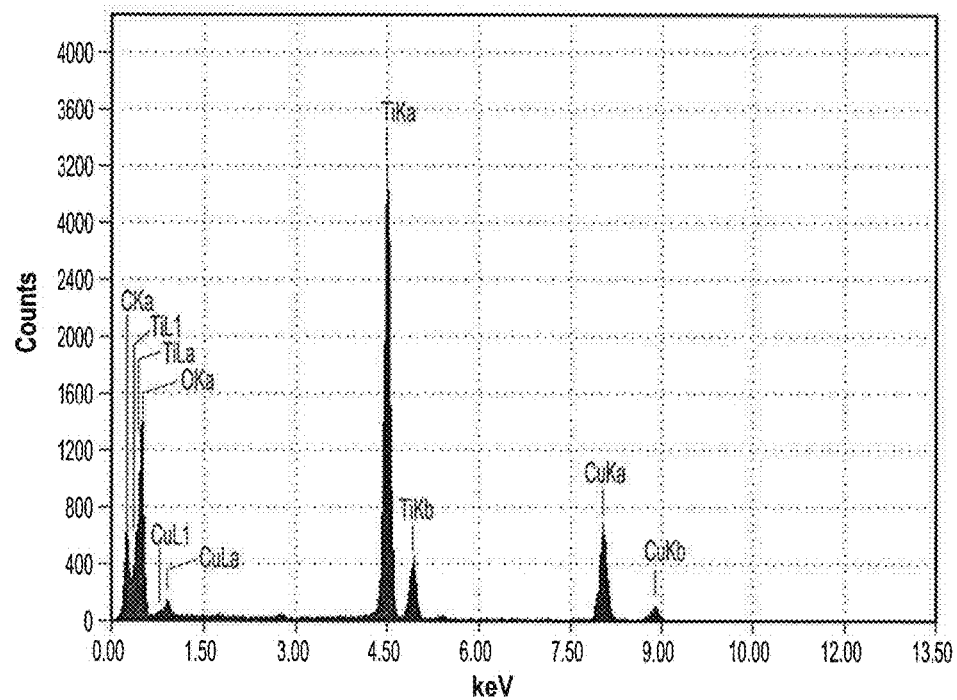
FIG. 3 shows the EDS analysis for the $TiO_2$ nanoparticles according to the present teachings.
Figure 5:
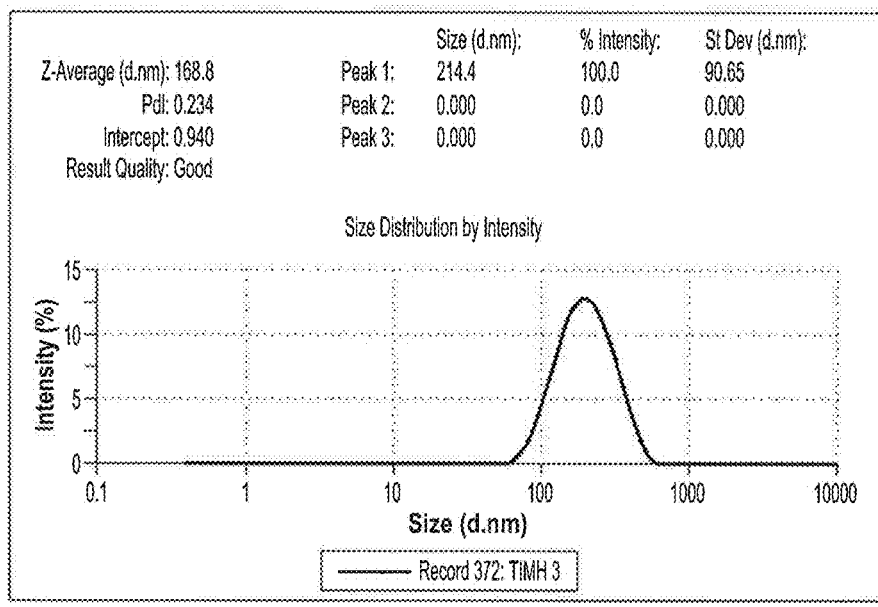
FIG. 5 is a graph showing the average particle size of the $TiO_2$ nanoparticles determined by Zetasizer analysis.

The resulting $TiO_2$ nanoparticles were characterized by performing powder X-ray diffraction (XRD) analysis using, Bruker D8 ADVANCE. The results showed that the structure was tetragonal. These results were in good agreement with JCPDS card number 21-1272. Peaks were observed at 25°, 38°, 48°, 53°, 55°, 62° and 75° (K. Ganapathi Rao et al, 2015). The XRD analysis of the synthesized $TiO_2$NPs is shown in FIG. 1. The morphology of the green titanium dioxide nanoparticles was characterized using transmission electron microscopy (TEM, JEM-1400, JEOL, Japan), as shown in FIGS. 2A-2C. Energy Dispersive Spectrometer (EDS) analysis was performed for confirmation of the elements in the resulting nanoparticles (EDS, JSM-7610F, JEOL, USA). As shown in FIG. 3, the EDS results confirmed the existence of elements of titanium and oxygen. As shown in FIG. 5, the average particle size of the titanium dioxide nanoparticles was determined to be 168.8 nm.

Example 2

Photocatalytic Measurements

Photocatalytic activity was evaluated under IN irradiation with a Rhodamine B dye. 20 ml of dye solution was put in a laboratory-scale cuvette and the titanium dioxide nanoparticle photocatalyst sample (2 mg) was dispersed inside the cuvette facing UV light at a distance of 5 cm from a UV light lamp. Optical absorption spectra were determined upon different light exposure durations using a UV/Vis spectrophotometer in order to monitor the rate of degradation by recording the reduction in absorption intensity of dye at the maximum wavelength ($\lambda$max=555 nm). The degradation efficiency (DE) was calculated using the following equation:

$$DE\% = (A_0 - A)/A_0 \times 100$$

where $A_0$ is the initial absorption and $A$ is the absorption intensity after UV irradiation.

Figure 4:
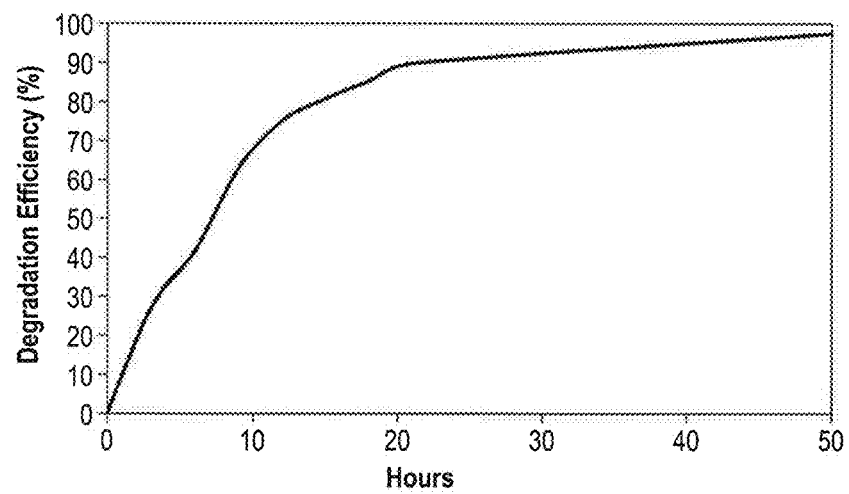
FIG. 4 is a graph showing the degradation efficiency of the $TiO_2$ nanoparticles under UV irradiation with Rhodamine B dye.

As expected, the green $TiO_2$ catalyst gave a good response under UV irradiation where the Rhodamine B dye removal % was about 100% (97.37179487%) after 50 h of irradiation as shown in FIG. 4. The excellent degradation efficiency by the resulting green $TiO_2$ nanoparticles can be attributed to an increase in number of active sites and photons absorbed by the catalyst. Accordingly, the $TiO_2$ nanoparticles can be used under direct solar irradiation in water treatment.

It is to be understood that the present subject matter is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of synthesizing titanium dioxide ($TiO_2$) nanoparticles, comprising:
   grinding *Cymbopogon proximis* grass to provide a ground grass;
   adding water to the ground grass to provide a mixture;
   filtering the mixture to obtain a filtrate;
   combining the filtrate with titanium (IV) isopropoxide (TTIP) to obtain a brown solution;
   heating the brown solution to obtain a paste;
   forming a powder from the paste;
   and calcinating the powder to provide the $TiO_2$ nanoparticles.

2. The method of synthesizing titanium dioxide ($TiO_2$) nanoparticles according to claim 1, wherein about 100 ml of the grass is ground to provide the ground grass.

3. The method of synthesizing titanium dioxide ($TiO_2$) nanoparticles according to claim 2, wherein about 100 ml of water is added to the ground grass.

4. The method of synthesizing titanium dioxide ($TiO_2$) nanoparticles according to claim 1, wherein the brown solution is heated at a temperature of about 80° C.

5. The method of synthesizing titanium dioxide ($TiO_2$) nanoparticles according to claim 1, wherein the powder is calcinated at a temperature of about 400° C.

6. A method of synthesizing titanium dioxide ($TiO_2$) nanoparticles, comprising:
   grinding *Cymbopogon proximis* grass to provide a ground grass;
   adding water to the ground grass to provide a mixture;
   filtering the mixture to obtain a filtrate;
   combining the filtrate with titanium (IV) isopropoxide (TTIP) to obtain a brown solution;
   heating the brown solution at a temperature of 80° C. to obtain a paste;
   forming a powder from the paste;
   and calcinating the powder at a temperature of about 400° C. to provide the $TiO_2$ nanoparticles.

\* \* \* \* \*